United States Patent [19]

Hanson et al.

[11] 4,096,428
[45] Jun. 20, 1978

[54] INSTRUMENT SUPPORTING TRANSFORMER UNIT

[75] Inventors: Larry E. Hanson; Raymond F. Schober, Jr., both of Topeka, Kans.; Merwin K. Alexander, St. Louis, Mo.

[73] Assignee: Optical Associates, Inc., St. Louis, Mo.

[21] Appl. No.: 730,635

[22] Filed: Oct. 7, 1976

[51] Int. Cl.² .................. A61B 19/02; A61C 19/02; H01M 10/46
[52] U.S. Cl. .......................... 320/2; 32/22; 312/209; 351/1
[58] Field of Search .............. 320/2, 3, 4, 5; 312/209; 351/1; 32/22; 128/303.1

[56] References Cited

U.S. PATENT DOCUMENTS

| | | | |
|---|---|---|---|
| 2,199,322 | 4/1940 | Skinner | 320/4 |
| 3,217,224 | 11/1965 | Sherwood | 320/2 |
| 3,371,260 | 2/1968 | Jackson et al. | 320/2 |
| 3,696,283 | 10/1972 | Ackley | 320/2 |
| 3,710,224 | 1/1973 | Daniels | 320/2 |
| 3,872,593 | 3/1975 | Thornton, Jr. et al. | 32/22 |

*Primary Examiner*—Robert J. Hickey
*Attorney, Agent, or Firm*—Paul M. Denk

[57] ABSTRACT

A transformer unit for supporting, preferably, medical instruments, while furnishing them with particular levels of electric charge to accommodate their operations or recharging. a mounting member supports the transformer, and a series of modular like instrument supports, each having a base that holds an instrument, and an inclined concaved side upon which the instrument rests, are secured together intermediate a pair side walls and connected to the mounting member. Electrical circuitry provides for the conductance of electrical charge to the transformer, and a series of circuitries, one provided in each instrument support, conveys the transformed charge to each support. Secondary circuitry within each support also conducts the stepped-down voltage to each support base where wiring of a medical instrument may be connected to attain its operation, or where a self contained instrument may be recharged as during nonusage.

19 Claims, 12 Drawing Figures

INSTRUMENT SUPPORTING TRANSFORMER UNIT

BACKGROUND OF THE INVENTION

This invention relates generally to a transformer, but more particularly is concerned with a medical instrument support incorporating transformation means that may conduct a variety of charges, preferably in a low voltage category, to provide for the selective operation of said instruments.

Various types of transformer devices have been available in the prior art, and for use, normally, for supplying generally reduced electrical charge to some low voltage operating appliance. Many of such transforming devices have found rather widespread contemporary usage as in providing charge to convenience appliances that can be readily used domestically. For example, the United States patent to Kircher, No. 3,473,859, discloses a support structure for a domestic appliance, which also includes means for conducting electrical charge to its support, as for use in recharging of a toothbrush holder. Although, it would not appear that any transformation means is provided within the disclosed device, this is usually necessary to provide recharging of low voltage operative power packs. And, the patent to Jackson, No. 3,371,260, discloses a similar type of toothbrush support with a recharger stand.

The current invention relates to the mounting of medical instruments upon a form of a plural instrument supporting bracket, and one which includes a transformer means so as to furnish a variety of the voltages needed for their attaining electrical operation, or re-charging of the instruments, as can be accommodated as this single unit. For example, in the practice of opthalmology, a variety of instruments are normally required by the practitioner, and generally localized near his patient examination center so that all of the instruments are within easy reach and readily available. One such control center is shown in the United States patent No. 3,724,931, wherein the control system is useful for both coordinating the lighting and instrument operation within an examination room. But, the particular structure for a control center, and its operation from a single transformation unit, as disclosed in the current invention, and one which is readily adaptable for ease of installation at the examination room, is not apparent from this earlier patented disclosure.

It is, therefore, the principal object of this invention to provide a medical instrument supporting transformer unit that includes its own transformation means for furnishing a variety of low voltages for operation of the particular, but plurality, of supported instruments.

Another object of this invention is to provide an instrument supporting unit that may accommodate either battery operated or hard wire connected medical instruments.

Another object of this invention is to provide a transformer unit for supporting medical instruments that includes individually connecting jacks associated with each instrument support and which can accommodate a plug for furnishing a level of a low voltage directly to a particular instrument.

An additional object of this invention is to provide an instrument supporting transformer unit that is modular in construction and can be assembled for holding a variety of differing types and separately energized instruments as are essential for specialized medical examination.

A further object of this invention is to provide a medical instrument supporting apparatus that may be either wall mounted, or rest upon a table surface.

A further object of this invention is to provide a compact size instrument supporting electrical power unit.

Another object of this invention is to provide a trasformer unit that supplies electrical energy to cord instruments, and which conduct of charge to said instruments is automatically curtailed when they are returned to their respective supports.

Another object of this invention is to provide an instrument bracket that includes its own transformer that may furnish a variety of voltages, generally in the lower range, to selective instrument supports, with each support having its own control for varying the potential to it.

Another object is to provide a modularized instrument support that is easy of fabriction and assembly due to the inter-cooperation between each modular supported unit as they are coupled together to meet the desired specifications.

These and other objects will become more apparent to those skilled in the art upon reviewing the summary of this invention, and undertaking a study of the description of the preferred embodiment in view of its drawings.

SUMMARY OF THE INVENTION

This invention contemplates the formation of a medical instrument support, as of the type used in dental, opthalmic, or other medical offices, and which includes its own transformer unit so as to supply select voltages, usually at low levels, to the various instruments being supported by the unit. Structurally, the unit includes a mounting member that provides a back support, and which has mounted thereon the transformer of this device. A series of side plates are also furnished, and a variety of modularized instrument supports may be coupled together, both electrically and structurally, intermediate the side supports secured with the mounting member, so as to form an integral housing that includes all of the components that function to provide both the support and electrical energy to and for the operation of the supported instruments. Electrically, the unit incorporates the transformer, as aforesaid, with the transformer having the standard alternating current charge conducted to it from a nearby receptacle. This charge is then converted, voltage-wise, and usually stepped down to within the vicinity of between about 2.5 to 12 volts potential, and which is conducted to each select supporting unit for use in energizing the various instruments. One or more of the supports may incorporate its own rheostat so that a fine adjustment can be made, generally within the aforesaid potential ranges, as may be required for its particular instrument. Each support includes a base member that cooperates with an inclined disposed concaved side so that the medical instrument, which normally may include a hand grip and be of cylindrical form, can be conveniently accommodated by the instrument support herein defined, with each support then having its base configured so as to accommodate the style of instrument required. For example, where the instrument is of the cord type, that is, hard wired to the voltage source, the base may include a slot through which the cord may attain clearance for integrally extending from the normally lower side of the supported instrument. These instruments, and more particularly their electrical cord, many times includes some form of a plug at their ends, and therefore, desirably a particular type of support for holding this type of instrument will provide a jack and into which the plug may be inserted for attaining electrical connection. Furthermore, the base of the support may include pressure sensitive switching means that will make or break electrical contact to the instrument as when the instrument may be removed or returned, respectively, from its place upon the support. Thus, a simple lifting of the instrument provides for the automatic operation of the same, while its return to the support breaks its electrical contact.

Other bases for the particular instrument supports may contain spaced contacts so as to provide for a recharging of the self contained style of instrument, one that possesses its own energy source in the form of an included battery,

BRIEF DESCRIPTION OF THE DRAWINGS

In the drawings, FIG. 1 provides a perspective view of the instrument supporting transformer unit of this invention.

DESCRIPTION OF THE PREFERRED EMBODIMENT

Figure 1:
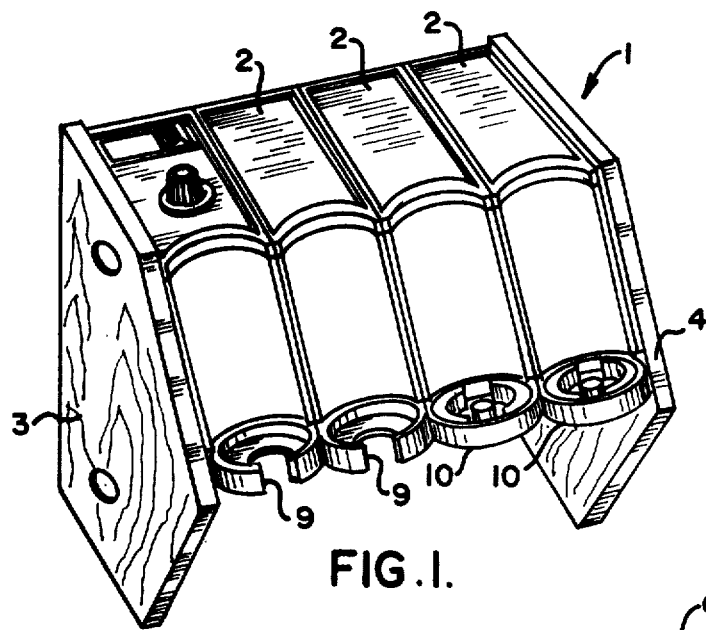
Figure 4:
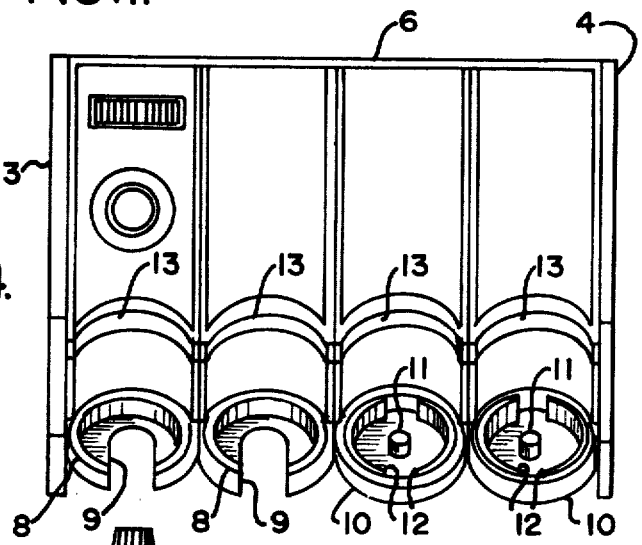
FIG. 4 provides a top view of the unit as shown in FIG. 1.

In referring to the drawings, and in particular FIGS. 1 through 4, there is disclosed the medical instrument supporting transformer unit 1 of this invention. This unit comprises a series of preferably modularly constructed instrument supports 2, four of them in number as being shown in these figures, and which supports are secured together both physically and electrically as by being embraced upon their side by means of a series of side plates 3 and 4. These supports and the side plates are connected to a mounting member 5, which structurally furnishes the back plate 6 and bottom plate 7 for the unit. The various supports 2 that make up the unit may vary in their construction, depending upon the style of instrumentation to be held, but as can be seen in these figures, the two left side supports include bases 8 that are slotted, as at 9, so that they may hold the hard or permanent wired instruments, thereby providing clearance for their respective cords through their formed slots 9. The other two instrument supports disclosed in this preferred embodiment include the type of bases 10 that incorporate recharging contacts 11 and 12 that are useful, when operative, for recharging of the battery operated and self contained medical instrument. As will be yet later described, each of these instrument supports are structured upwards from their bases having concaved surfaces, as at 13, so as to snugly embrace the sides of the various supported instruments.

Figure 6:
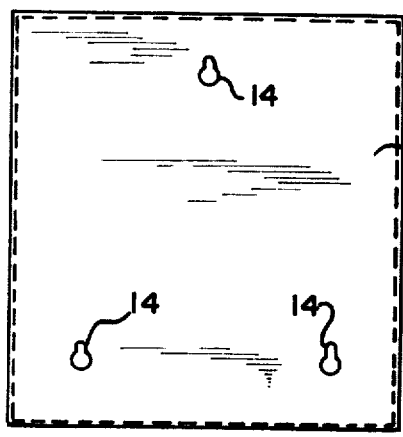
FIG. 6 provides a back view of the mounting means of this invention, as shown in FIG. 5.
Figure 5:
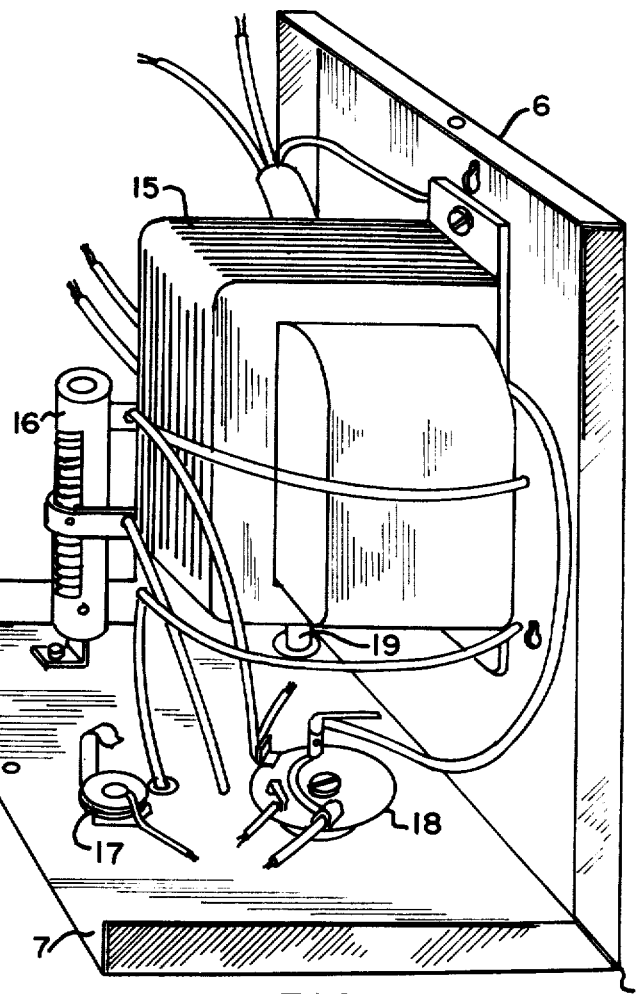
FIG. 5 provides a view of the mounting means and its transformer, and other electrical devices, as incorporated within this invention.
Figure 7:
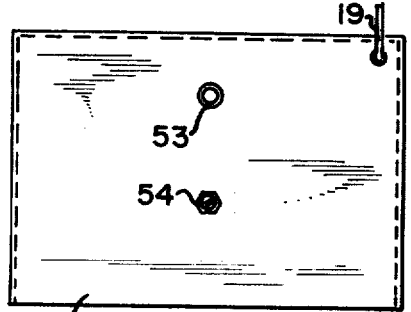
FIG. 7 provides a bottom view of the said mounting means.

FIGS. 5 through 7 display various mounting means, and some of the electrical components utilized in this invention. As can be seen, the mounting means 5, formed by the back plate 6 and the bottom plate 7 comprises a rather wide ranging angulated member, with the back plate having a series of apertures 14 therethrough to accommodate mounting screws as when the unit is fastened or suspended upon a wall. In addition, there is disclosed the transformer 15 that mounts to the interior of the back plate 6, therefore leaving sufficient clearance at its front to accommodate the various instrument supports 2 when they are secured into the unit. The transformer utilized in this invention may be of the conventional style, including the primary and secondary windings, and usually will be of the step down variety so as to decrease the standard 110 or other voltage down to the vicinity of 2.5 to 12 volts, as for example, when this unit is utilized in conjunction with low voltage operating instruments. Although, other voltages may be supplied from from this type of a unit, as through the use of a transformer, so as to supply the potential required for any type of instrument that may be accommodated by this type of an invention.

Also physically disclosed in FIG. 5 is a variable resistor 16, which is useful in providing a more finer control in the voltage desired from this unit, in addition to a plug in jack 17, and into which one of the hard wired instruments may be connected so as to provide charge for its operation. Furthermore, there is also disclosed a switch 18 that may be useful for providing voltage selection from the secondary of the transformer so as to provide a quick and rough setting of the voltage down to a particular approximate level, before the variable resistant 16 may be manipulated to provide for a fine adjustment in the desired potential. In addition, and as can be seen both in FIGS. 5 and 7, the electrical cord 19 that supplies the basic voltage and current to the transformer primary is disclosed extending from the bottom panel 7, so that it may be connected into a common wall socket.

Figure 3:
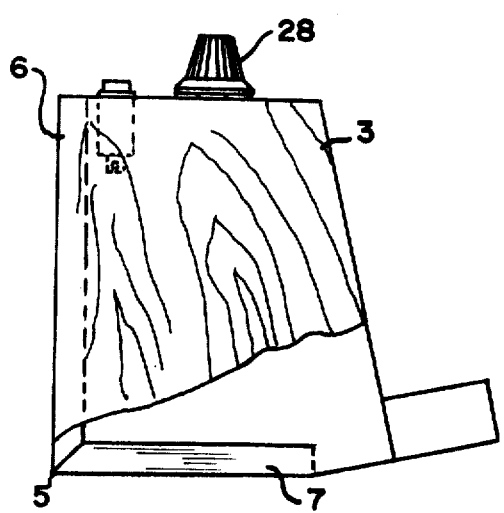
FIG. 3 provides a side view of the unit as shown in FIG. 1.
Figure 2:
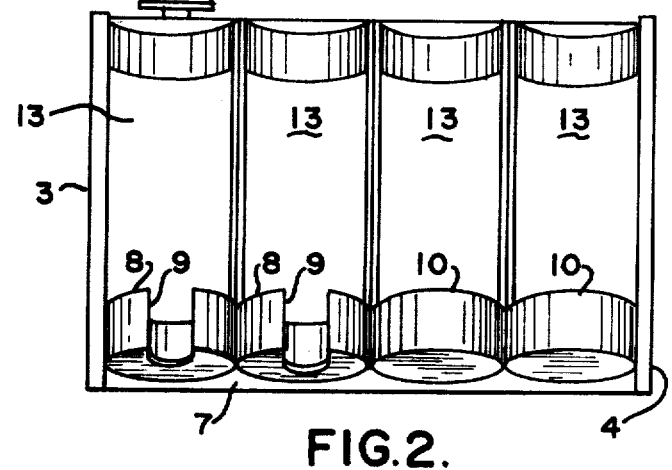
FIG. 2 provides a front view of the unit as shown in FIG. 1.
Figure 9:
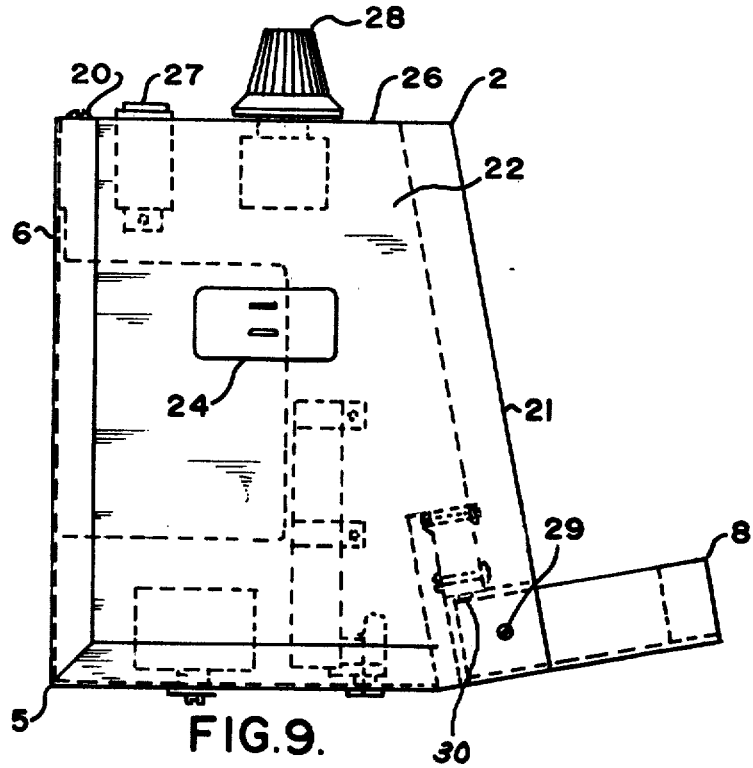
FIG. 9 discloses a side view of one of the modular instrument supports that makes up the transformer unit of this invention.
Figure 10:
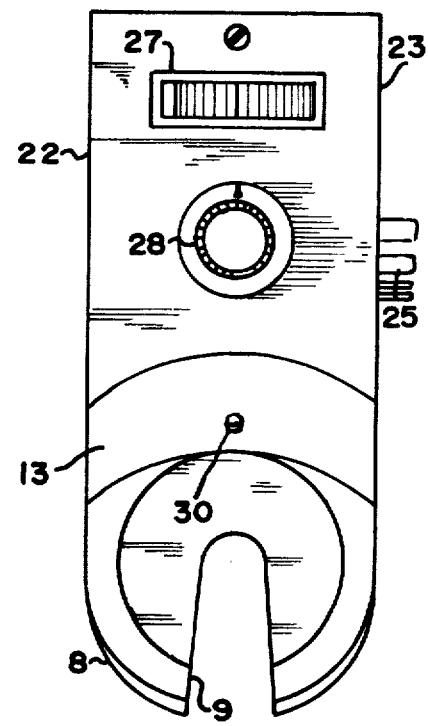
FIG. 10 provides a top view of the support disclosed in FIG. 9.

FIGS. 9 and 10 disclose one of the modular like instrument supports 2, which in this particular instance, contains many of the master controls that are useful for providing the initiation of the operations of this unit, such as the left end support also shown in FIGS. 1 through 3. As can be seen, the unit 2 is secured by means of the fastener 20 to the back panel 6 of the mounting member 5. Each support includes an inclined frontal disposed surface 21, which is concaved, as previously shown at 13, and also includes side walls 22 and 23, being relatively flat in configuration, so that these modular supports may be placed in adjacency when a plurality of them are formed into an operating unit. As previously commented, the unit, as shown at 1, includes four such modular supports 2. Provided upon the opposite sides 22 and 23 of each support are electrical receptacle and plug 24 and 25, respectively, which may comprise the usual style of Cinch-Jones plug and receptacle, or any other combination of plug and receptacle so as to provide for electrical connection between each adjacent support, and a conduit for transfer of charge between said supports. Projecting through the top wall 26 of the unit 2 is an off-on switch 27, useful for initiating the electrical operations of the unit, and also included is a knob 28 that provides for manual control of the rheostat setting of the various voltage levels for operation of this device.

Projecting from the front side 21 of each modular support is the base member 8, as previously described, being secured in place by means of pivot screws 29 at opposite sides of member 8. Each base is preferably constructed of an annular shape so as to accommodate the bottom of the various medical instruments currently available upon the market and being used by medical technicians, and in addition, the cord slot 9 is provided cut into the base member. Also, projecting from the base of the support is the stem 30 of a micro switch, and which is of the type that when it is depressed by having a medical instrument rested upon a support causes a break in the circuit condition so that electrical energy will be discontinued to the instrument. On the other hand, when the instrument is removed, the stem 30 of the micro switch will be allowed under spring pressure to protrude to achieve a make circuit condition so that electrical energy will be conducted to the instrument and provide for its immediate operation. This occurs when the instrument is removed and allows the base member 8 to pivot around screws 29 so that the switch 30 may actuate circuitry.

An alternate form of base 10, as briefly previously described, is of the recharging type, and may be located in lieu of the base 8 in conjunction with any particular modularized instrument support 2, and thereby function as a means for recharging of a self-contained battery operated instrument. Such a base is more accurately shown in FIGS. 11 and 12, and also comprises a form of annularized member, having an aperture 31 disposed centrally therethrough, and into which the lower handle portion of a medical instrument may be inserted. A pair of contacts 32 are spring biased, by means of their springs 33 as recessed within the sides of the cavity 31, and are normally biased outwardly towards the center of the same. Hence, when the handle of an instrument is inserted within the aperture 31, it pushes the arcuate contacts 32 into a widening condition but yet snugly biasing against the downward portion of the instrument handle which normally have contacts located at these locations for recharging purposes. In addition, a center tap 34 is provided for completing circuitry to the battery pack of the rechargable instrument. The contacts 32 may be foil faced upon their interior so as to insure adequate electrical contact with the instrument. As will be subsequently described, all of these contacts are coupled within the electrical circuitry of this transformer unit so that a precise charge, for recharging purposes, can be conducted to the instrument, as when it is not being used and resting upon its base member 10.

Figure 8:
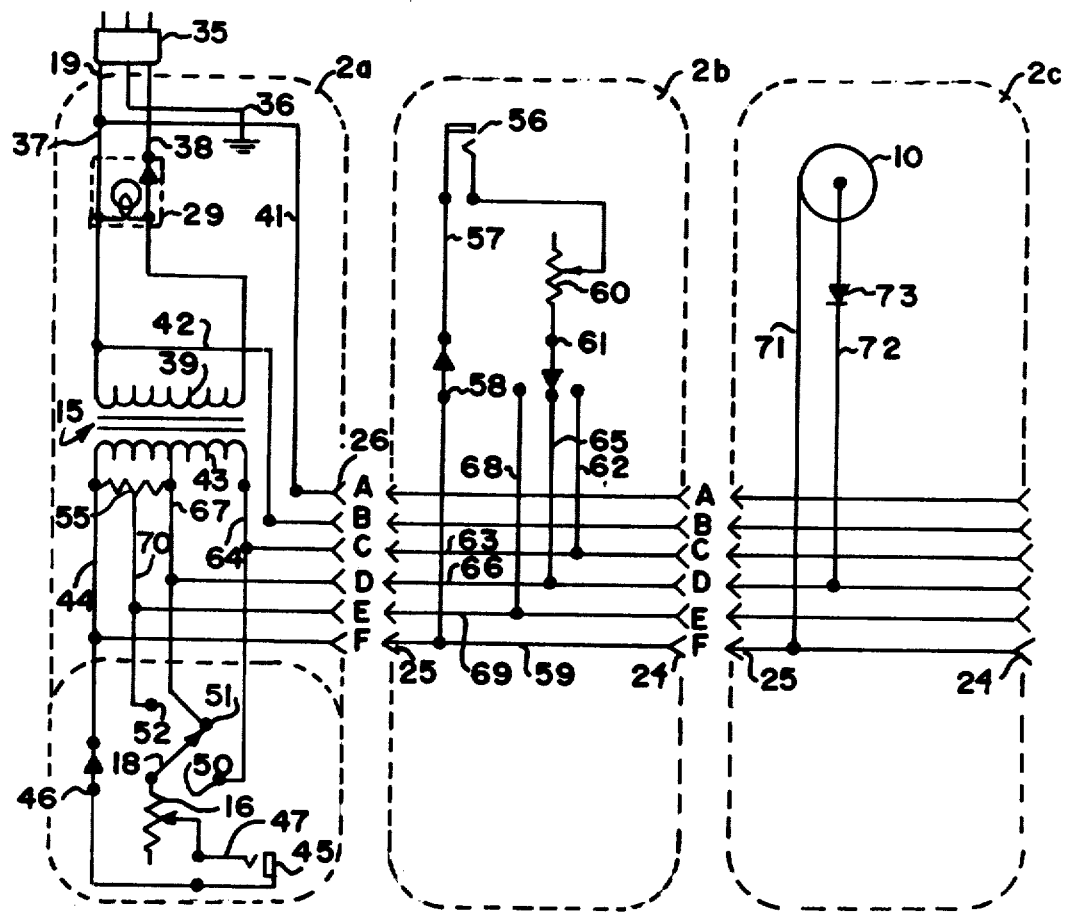
FIG. 8 discloses a circuit diagram for attaining electrical operations of this invention.

Electrical circuitry for this invention is disclosed in FIG. 8. The circuitry for three such modular supports 2a, 2b and 2c, are shown, and it can be seen that each of these supports, with the exception of the left side wall of the master support 2a, includes the plugs 25 and receptacles 24 on alternate sides. Thus, these supports can be plug together to provide the series connection and conduct of charge from the master unit to the adjacent instrument supports.

The master support includes the male plug 35 that may secure to a wall outlet, and it connects by means of a cord 19 internally of its structure. One wire of the cord may be grounded, as at 36, while the other electrical lines 37 and 38 are wired to a lighted power switch 27, as previously described. Then, the wires 37 and 38 continue to their connection with the primary side 39 of the transformer 15. Connecting with the circuit line 37 is a branch line 41 that may conduct line charge through the A pins of the plug and receptacles 25 and 24, as previously explained. In addition, another circuit line 42 also connects with the circuit line 37 for conducting electrical line charge through the B pins of the same plugs and receptacles. A series of circuit lines connect to the secondary 43 of the transformer, with one such line 44 extending from one side of the said secondary and connecting with the plug-in jack 45 of the master unit 2. A micro switch 46 is contained within this circuit line, and is of the type that is normally closed when at rest, but that when an instrument may be set upon its switch stem 30, as previously described, causes on open circuit condition so as to discontinue the flow of charge to the jack 45. The other side of the jack 45 includes its circuit line 47 that connects with the variable resistance or rheostat 16, which may be controlled by the knob 28, such having been previously defined projecting above this instrument support. This particular rheostat, as will be seen, provides for a fine adjustment in the voltage output from the transformer to a range that is more precisely required for the operation of a particular instrument, generally somewhere in the vicinity of 2.5 to 12 volts. The rheostat 16 connects with a switch 18 that can provide for a rapid adjustment in the output of the secondary of the transformer between a full voltage, half voltage, or a fractional voltage depending upon its setting with either of its contacts 50, 51 or 52, respectively. It should be commented that instrument connection may be made with the jack 45 by insertion of a corded plug from an electrical instrument into the receptacle 17 provided at the bottom of the base plate 7. In addition, the switch 18 can be adjusted between its settings by manipulation of the voltage selector screw 54 which projects through the bottom of the base plate 7 of the instrument. See FIG. 7. When the switch 18 is in contact with its pin 50, full secondary voltage output can be attained from the transformer through the jack 45. When the switch is adjusted to its pin 51, a half voltage output can be attained. And, when the switch is connected to its pin 52, the variable resistor circuitry 55 can be adjusted so as to provide for a fine setting at a lower voltage level from this secondary of the transformer 15. Any of these voltages can be selectively acquired through a plug in with the jack 45, by insertion within the slot 53 provided at the bottom of the master unit 2.

As previously commented, the instruments 2b and 2c are connected in series with the master support 2a through the agency of the connection of their various pins A through F of the receptacles 24 and the plugs 25. With regard to the instrument support 2b, it is of the type that incorporates a plug in jack 56, and into which a cord of a medical instrument may be plugged for electrical operation. One side of the jack is connected by the circuit line 57, having an off-on switch 58, either of the manual type or of the spring loaded contact type, provided therein so as to allow for the turn on or off of the power. The circuit line 57 further connects with the circuit line 59, which in turn connects through pin number F for coupling with the circuit line 44 at one side of the secondary of the transformer 15. The other side of the jack 56 connects through a variable resistor 60, and this part of the circuitry also includes a selector switch 61 which can tap into the secondary 43 of the transformer at three locations, as along circuit line 62 which connects to the circuit line 63, through the pin C of the receptacle, and then connects with the circuit line 64 at the full voltage side of the secondary of said transformer. The selector switch 61 may also connect through the circuit line 65, which connects to the circuit line 66 and through the B pin of the receptacle 25, for connection with the circuit line 67 that provides a center tap from the secondary of the transformer 15. In addition, a third position for the selector switch 61 includes the circuit line 68, which connects with the circuit line 69, through the E pin of the receptacle 25, and then connects with the circuit line 70 of the variable resistance 55, wherein a lower and more precise potential may be tapped for providing electrical operations of the medical instrument associated with the support 2b.

Figure 11:
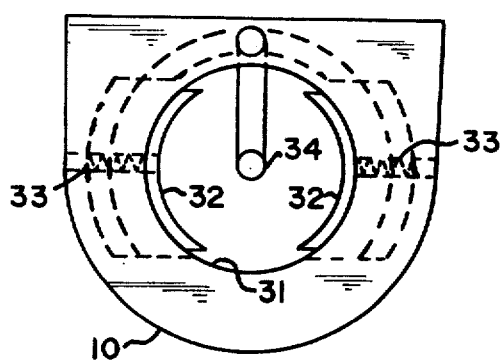
FIG. 11 provides a plan view of one of the support bases, that type which is used for recharging of the battery operated medical instrument.
Figure 12:
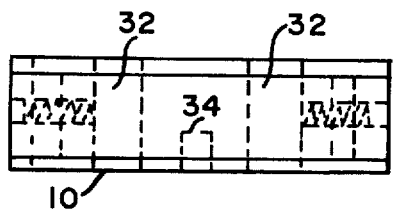
FIG. 12 provides a front view of the support base as shown in FIG. 11.

The final support, namely, the instrument support 2c, disclosed in the circuit diagram of FIG. 8, provides the type of circuitry that is useful for recharging of a self contained medical instrument, of the type that runs from an inherent battery power pack. In this device, the support, or its base, such as the base 10 as previously described with respect to FIG. 11, is connected by a pair of circuit lines 71 and 72 through the circuit lines 59 and 66, respectively, by way of receptacles 24 and plugs 25. Thus, potential from the center tab, as along circuit line 67 from the secondary 43 of the transformer 15 is provided to the base 10. And, since battery power is always of the direct current type, by necessity, the charge to the base 10 must be either a direct current, or a rectified alternating current. Therefore, a diode 73 is provided in one of the circuit lines, such as shown in the circuit line 72, so as to provide a half wave rectified current for use in conjunction with the charging base 10. And, when an instrument is placed and inserted upon its base 10, it can be recharged in the manner as previously described with respect to the operations of this base as analyzed with respect to FIGS. 11 and 12.

Various modifications in the instrument supporting transformer unit of this invention may occur to those skilled in the art upon reviewing this subject matter of this invention. Any such variations or modifications that full within the spirit and scope of this invention, and which are encompassed by the claims to patent protection appended hereto, are intended to be protected in any United States patent issuing hereon. The description of the preferred embodiment is set forth for illustrative purposes only, and is not meant to be limiting of the scope of this invention.

Having thus described the invention what is claimed and desired to be secured by Letters Patent is:

1. A transformer unit for use in furnishing voltage to one or more electrically operated medical instruments comprising a mounting means, a transformer means incorporating both primary and secondary windings supported by said mounting means, a series of instrument supports held by the mounting means and electrically coupled with the transformer for furnishing an electrical charge to each support for selective energization of certain of its respective instruments, said transformer capable of electrically coupling to a source of energy for energizing the unit, at least one of said supports including one of charging means and wiring means for respective selective recharging and electrical wiring its supported instrument, and a plurality of electrical connecting means provided upon each instrument support for their electrical coupling together and to the transformer means for furnishing selected variable voltages to each support for providing recharging or energization of its respectively held medical instrument.

2. The invention of claim 1 wherein certain of said supports are provided with charging means for recharging of their respective instruments from the transformer means, and other of said supports include wiring means for coupling with their supported instruments for directly furnishing them with electrical energy.

3. The invention of claim 2 and including multiple wiring means interconnecting between the said transformer means and each support and furnishing multi voltage levels to each support for effecting one of said recharging and energization at preselected variable voltage levels for each held medical instrument.

4. The invention of claim 3 wherein each instrument support comprises an independent instrument holding unit that is capable of electrically coupling with the adjacent like support, with all of said supports being arranged into an integral single transformer means charged unit.

5. The invention of claim 4 wherein each instrument support includes electrical coupling means provided upon its sides and disposed for electrically connecting with its adjacent supports, each support having charge transferring circuitry therein, with all of said instrument supports thereby being electrically connected with said transformer means.

6. The invention of claim 5 wherein each such electrical coupling means and charge transferring circuitry electrically connects each support in series with the transformer means.

7. The invention of claim 6 wherein each instrument support includes additional electrical circuitry connecting with its said support transferring circuitry, said additional circuitry provided for furnishing electrical charge to the supported instrument.

8. The invention of claim 7 wherein the additional electrical circuitry furnishing electrical energy to the supported instrument is parallel connected with respect to the said transformer means.

9. The invention of claim 3 wherein each charging support includes a first contact point electrically connecting to one tap of the transformer means secondary, and another contact point electrically connecting to another tap of the transformer means secondary, the two contact points provided for conducting electrical charge at a preselected voltage to an instrument for inducing its recharging.

10. The invention of claim 9 wherein each support includes an annular base incorporating the contact points, said base disposed for providing a lower support for a held instrument, each support also including an integral inclined concaved surface for embracing the side of any supported instrument.

11. The invention of claim 3 wherein each electrical wiring support includes an annular base having a slot therein for accommodating the wiring means of a supported instrument, said base disposed for providing a lower support for a held instrument, each support also including an integral inclined concaved surface for embracing the side of any supported instrument.

12. The invention of claim 3 and including a rheostat means connecting intermediate the transformer means and at least one charged support for varying the voltage conducted to the said support.

13. The invention of claim 12 and including said rheostat including an adjustment knob, said knob disposed through a support and allowing for an adjustment in the voltage provided at the associated instrument support.

14. The invention of claim 3 and including side walls connecting with the adjacent instrument supports as arranged intermediate thereof, said side walls providing for lateral closure for the transformer unit.

15. The invention of claim 7 and including a jack provided upon the bottom of at least one electrically wired support and being electrically connected to said additional circuitry, said jack being disposed for reception of the plug of any an associated instrument for furnishing it with electric energy.

16. The invention of claim 3 and including a series of rheostat means connecting intermediate the transformer secondary windings and at least one charged support for varying the voltages furnished to the said instrument support.

17. The invention of claim 3 wherein said mounting means is wall mountable.

18. The invention of claim 11 wherein said base is pivotally mounted to the support to regulate the conduct of charge to the held instrument.

19. The invention of claim 10 wherein said base is pivotally mounted to the support to regulate the conduct of charge to the held instrument.

* * * * *